United States Patent

Jarman et al.

Patent Number: 5,891,024
Date of Patent: Apr. 6, 1999

[54] TWO STAGE CALIBRATION AND ANALYTE MEASUREMENT SCHEME FOR SPECTROPHOTOMERIC ANALYSIS

[75] Inventors: Kristin Jarman, Lafayette; Jonas A. Pologe, Boulder, both of Colo.

[73] Assignee: Ohmeda Inc., Louisville, Colo.

[21] Appl. No.: 835,289

[22] Filed: Apr. 9, 1997

[51] Int. Cl.⁶ .................................................. A61B 5/00
[52] U.S. Cl. ................................. 600/323; 356/41
[58] Field of Search .................... 600/310, 322, 600/323, 326, 328, 473, 476; 356/39, 41

[56] References Cited

U.S. PATENT DOCUMENTS

| | | | |
|---|---|---|---|
| 3,638,640 | 2/1972 | Shaw | 128/2 R |
| 4,266,554 | 5/1981 | Hamaguri | 128/633 |
| 4,407,290 | 10/1983 | Wilber | 128/633 |
| 4,446,871 | 5/1984 | Imura | 128/633 |
| 4,603,700 | 8/1986 | Nichols et al. | 128/633 |
| 4,714,341 | 12/1987 | Hamaguri et al. | 356/41 |
| 4,800,885 | 1/1989 | Johnson | 128/633 |
| 4,819,646 | 4/1989 | Cheung et al. | 128/633 |
| 4,819,752 | 4/1989 | Zelin | 128/633 |
| 4,832,484 | 5/1989 | Aoyagi et al. | 356/41 |
| 4,846,183 | 7/1989 | Martin | 128/633 |
| 4,854,699 | 8/1989 | Edgar, Jr. | 356/41 |
| 4,867,557 | 9/1989 | Takatani et al. | 356/41 |
| 4,883,353 | 11/1989 | Hausman et al. | 356/41 |
| 4,907,876 | 3/1990 | Suzukik et al. | 356/41 |
| 5,057,695 | 10/1991 | Hirao et al. | 250/575 |
| 5,061,632 | 10/1991 | Shepherd et al. | 436/66 |
| 5,113,861 | 5/1992 | Rother | 128/633 |
| 5,149,503 | 9/1992 | Kohno et al. | 422/82.05 |
| 5,188,108 | 2/1993 | Secker | 128/633 |
| 5,277,181 | 1/1994 | Mendelson et al. | 128/633 |
| 5,285,783 | 2/1994 | Secker | 128/633 |
| 5,299,570 | 4/1994 | Hatschek | 128/633 |
| 5,343,818 | 9/1994 | McCarthy et al. | 128/633 |
| 5,349,952 | 9/1994 | McCarthy et al. | 128/633 |
| 5,355,880 | 10/1994 | Thomas et al. | 600/326 |
| 5,385,143 | 1/1995 | Aoyagi | 128/633 |
| 5,431,159 | 7/1995 | Baker et al. | 128/633 |
| 5,448,991 | 9/1995 | Polson et al. | 128/633 |
| 5,692,503 | 12/1997 | Kuestner | 600/322 |

OTHER PUBLICATIONS

Webb–Warin Lung Institut—Clinical Pulse Oximetry by Thomas L. Petty, M.D. (1986).

Primary Examiner—Max Hindenburg
Assistant Examiner—Eric F. Winakur
Attorney, Agent, or Firm—Holme Roberts & Owen LLP

[57] ABSTRACT

A two-stage statistical calibration and measurement method and system is disclosed for performing photoplethysmographic measurement of blood analyte concentrations. Concentrations in a tissue sample of MetHb, $O_2$Hb, RHb and COHb are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes $O_2$Hb, RHb and COHb (in a second stage). That is, by eliminating one "unknown" from the system of equations, these remaining analytes can be calculated with increased accuracy. Each stage is performed using data obtained by transmitting light through the tissue sample (typically a finger or earlobe). The transmitted light is generated by four discrete light emitters, each emitter having a distinct spectral content.

24 Claims, 5 Drawing Sheets

TWO STAGE CALIBRATION AND ANALYTE MEASUREMENT SCHEME FOR SPECTROPHOTOMERIC ANALYSIS

FIELD OF THE INVENTION

The present invention relates to spectrophotometric analysis for measuring the concentrations of each of a plurality of analytes in a sample. More particularly, the present invention relates to photoplethysmographic analysis for determining concentrations of various hemoglobin species in blood.

BACKGROUND OF THE INVENTION

In spectrophotometric analysis, estimates of the concentration of various analytes in a sample are determined by (a) transmitting light from one or more emitters through the sample, (b) measuring the amount of light transmitted through the sample from each emitter, and (c) using the measured light in a calibration equation to obtain the analyte estimates. To maximize the information obtained from the sample-under-test, each emitter typically emits light having distinct spectral content and center wavelength.

Typically, theoretical relationships along with statistical regression techniques are used to develop a calibration equation. In particular, a pre-specified equation form is chosen which relates the measured light to the analytes of interest. Constants present in this equation, called calibration coefficients, are then determined from a test collection of measured light vectors corresponding to known quantities of the analytes, as one skilled in the art will understand. However, to effectively utilize such a methodology the analytes must be distinguishable at the center wavelengths of light used. That is, the contribution of any one analyte to the measured light from all emitters cannot be a linear combination of the corresponding contributions of one or more other analytes. Moreover, no subcollection of the analytes should absorb light so strongly that absorption of light due to other analytes in the sample cannot be measured. Additionally, to cost-effectively provide such spectrophotometric analysis, there is an emphasis on minimizing the number of emitters used. It is well known, however, that there must be at least as many distinct emitters (each with its own unique spectral content) used as there are analytes whose concentrations are to be determined. Furthermore, in order to obtain accurate concentration estimates, additional emitters are often used, thereby creating a mathematically over-determined system. Thus, in conventional spectrophotometry, there is a cost versus accuracy tradeoff, wherein both cost and accuracy increase with an increase in the number of emitters used in such systems.

Accordingly, it would be advantageous to have a method and system for increasing the accuracy of such spectrophotometric analysis without incurring the cost associated with increasing the number of emitters. In photoplethysmography, maintaining a high degree of accuracy at a low cost is particularly important. That is, a high degree of accuracy is required in order to ensure patient safety and alert the clinician of critical situations, while cost containment pressures on the medical community necessitate low cost monitoring devices.

SUMMARY OF THE INVENTION

The present invention is an improved method and system for spectrophotometric analysis, and in particular, for estimating the concentration of each analyte of a set of analytes in a tissue sample. The present invention utilizes measurements of transmitted light from each of a plurality of electro-optical channels, wherein each channel: (a) emits light (e.g., by a light emitting diode (LED) or laser diode) having a distinct spectral content (and typically a unique center wavelength) into the tissue sample, and (b) detects the intensity of light transmitted through the tissue sample. Accordingly, the intensity of light transmitted from each emitter through the tissue sample and measured by a photodetector can be used in a calibration equation to estimate the concentration of each blood analyte in the tissue sample.

The present invention provides increased accuracy for estimating the concentrations of the analytes within a tissue sample while minimizing the number of channels used (e.g., minimizing the number of emitters with distinct spectral contents used). In one embodiment of the present invention, the distinct spectral contents of the light transmitted by each emitter have a fairly narrow band and have center wavelengths in the range of 600 nanometers (nm) to 1000 nanometers (nm). However, it is also within the scope of the present invention that other spectral regions may be utilized such as 500–600 nm and 1000–1400 nm.

The present invention increases the accuracy of estimating analyte concentrations through a two-stage analysis. This two-stage analysis is useful when the analytes to be measured absorb the emitted light in the following manner: for a first collection of one or more of the analytes to be measured, the absorption characteristics for analytes of this collection are sufficiently distinct from one another and from the remaining analytes, that accurate estimates may be derived for these analytes regardless of the concentrations of the other analytes. Accordingly, the first stage of the present invention determines an estimated concentration for each analyte in the first collection of analytes without considering the concentrations of the remaining analytes.

In a second stage of the two-stage analysis, the computed concentration for each analyte in the first collection is assumed to be accurate, and the concentrations of the remaining analytes are determined by exploiting a mathematically over-determined system. Because in the second stage there are fewer analyte concentrations to be determined than there are emitters used, an increase in accuracy may be obtained beyond, for example, simply utilizing an exactly determined system having the same number of unknown analyte concentrations as there are emitters.

Accordingly, it is an aspect of the present invention to utilize statistical techniques, such as linear or non-linear least squares regression, in two distinct stages for increasing analyte concentration estimation accuracy.

In photoplethysmography, the two-stage computational technique of the present invention is particularly useful. For example, in one embodiment of the present invention the novel two-stage computational technique is used to more accurately measure the concentration (as a percentage of total hemoglobin) of oxyhemoglobin ($O_2Hb$), deoxyhemoglobin (RHb), carboxyhemoglobin (COHb) and methemoglobin (MetHb) by obtaining light measurements at four distinct center wavelengths (within the range of 600 nm to 1000 nm) transmitted through tissue of a patient. Since MetHb can be estimated accurately regardless of the concentration of $O_2HB$, RHb and COHb, the first collection of analytes includes only MetHb so that in the first stage, MetHb is determined using calibration coefficients derived from linear or non-linear least squares regression. Subsequently, in the second stage, the concentrations of the other three hemoglobin types are computed by utilizing calibration coefficients derived from least squares regression on samples having a MetHb concentration the same (or substantially the same) as the concentration computed in the first stage. Note that the present two-stage technique is especially useful in the present context since the presence of significant amounts of MetHb interferes with the ability to estimate the concentrations of the other types of hemoglobin.

Moreover, it is a further aspect of the present invention to perform tests on the results from the first stage prior to utilizing these results in the second stage. Accordingly, if the values from the first stage are deemed to be outside a predetermined range, then it is a further aspect of the present invention to then use alternative calibration equations for estimating the remaining analyte concentrations. Referring once again to photoplethysmography, the present invention determines whether the measured MetHb concentration is within a predetermined range before the estimated concentration of this analyte is used in the second stage of calculations. In particular, since it is known that MetHb typically varies within a relatively narrow range of approximately 0 to 1% of total hemoglobin, a value of greater than or equal to 1% of the total hemoglobin is considered above normal. In this case, alternative calibration equations are used to compute the $O_2Hb$, RHb, and COHb concentrations.

As one skilled in the art will understand, the method of the present invention may also be used to enhance spectrophotometric analysis where the system is initially overdetermined. Therefore, it is within the scope of the present invention that this method provides increased accuracy in estimating any N analytes ($N \geq 2$) using N+M emitters ($M \geq 0$). In the example discussed above, if five or more emitters are used to estimate the concentrations of the four hemoglobin species MetHb, $O_2Hb$, RHb, and COHb, then the system is initially over-determined. For the first collection having only MetHb and the remaining collection having $O_2Hb$, RHb and COHb, additional accuracy in estimating the concentrations of $O_2Hb$, RHb and COHb is provided once the concentration of MetHb has been estimated according to the first stage of the present invention.

Other features and benefits of the present invention will become apparent from the detailed description with the accompanying figures contained hereinafter.

DETAILED DESCRIPTION OF THE PREFERRED EMBODIMENT

Before describing the steps of the present invention in detail, a brief description of the computational analysis used in photoplethysmography is provided. In particular, photoplethysmography utilizes a plurality of electro-optical channels for communicating or transmitting light through a tissue-under-test. Each channel includes an emitter that transmits light having a distinct spectral content. The light emitted on each channel through the tissue-under-test is subsequently detected by a photodetector. Since the tissue-under-test is typically a finger, earlobe, or other well vascularized tissue, the light detected by the photodetector on each channel can be characterized as a waveform having two components. The first waveform component varies with the pulsation of the patient's blood (this component denoted the AC component). The second component is the nonvarying contribution to the transmitted light level and corresponds to the total light passing through the tissues of the patient without being absorbed or scattered (this latter component denoted the DC component). For each such channel, a differential absorption is approximated as:

$$dA \cong \Delta A = \frac{\Delta I}{I} \quad (1)$$

wherein $\Delta I$ is a difference of transmitted light at two time instants and I is a measurement of the instantaneous transmitted light intensity obtained from the DC component.

Since such differential absorptions are computed, from measurements taken virtually simultaneously on each channel, these differentials may be used to estimate the concentration of various analytes in the patient's blood. Accordingly, various computational techniques have been utilized for computing analyte concentrations from such differential absorptions. For example, statistical regression techniques may be used to determine the calibration coefficients equation which uses differential absorptions for in order to estimate analyte concentrations, as one skilled in the art will understand. For example, two such channels can be used to compute two differential absorptions, $dA_1$ and $dA_2$, in order to estimate relative concentrations of $O_2Hb$ and RHb, where the predetermined function is given by:

$$xHb = aR^2 + bR + c, \quad (2)$$

wherein $$R = \frac{dA_1}{dA_2} \text{ ; and}$$

a, b, and c are regression coefficients determined from linear least squares regression, and xHb refers to $O_2Hb$ or RHb. Alternatively, the following function can be also used:

$$xHb = \frac{a_1 dA_1 + a_2 dA_2}{b_1 dA_1 + b_2 dA_2} \quad (3)$$

wherein $a_1$, $a_2$, $b_1$, $b_2$ are the calibration coefficients. Accordingly, as one skilled in the art will understand, in utilizing two differential absorption measurements, $dA_1$ and $dA_2$, either of the above functions, i.e., equation (2) or (3), can be used to provide estimates for the concentrations of the two analytes.

Note, however, it is not necessary to limit such estimation techniques to two differential absorption measurements. In particular, by providing a larger number of channels for transmitting light having additional distinct spectral contents, a larger number of analyte concentrations may be estimated. For example, in one embodiment of the present invention, the concentrations of the four hemoglobin species: $O_2Hb$, RHb, COHb and MetHb, are estimated by using at least four channels. Accordingly, if there are exactly four channels, then four differential absorption measurements $dA_1$, $dA_2$, $dA_3$ and $dA_4$ may be measured for a test sample and combined in a predetermined equation for estimating the concentrations of each of the four hemoglobin types. That is, extending function (3) above to four differential absorption measurements, the following equation is obtained:

$$xHb = \frac{a_1 dA_1 + a_2 dA_2 + a_3 dA_3 + a_4 dA_4}{b_1 dA_1 + b_2 dA_2 + b_3 dA_3 + b_4 dA_4} \quad (4)$$

where xHb can be any one of the four hemoglobin species: $O_2Hb$, RHb, COHb, MetHb, and the constants $a_1$, $a_2$, $a_3$, $a_4$, $b_1$, $b_2$, $b_3$, and $b_4$ are calibration coefficients determined by nonlinear least squares regression. (The constants $a_1$, $a_2$, $a_3$, $a_4$, $b_1$, $b_2$, $b_3$, and $b_4$ have distinct values for each of the four hemoglobin species.)

Figure 1A:
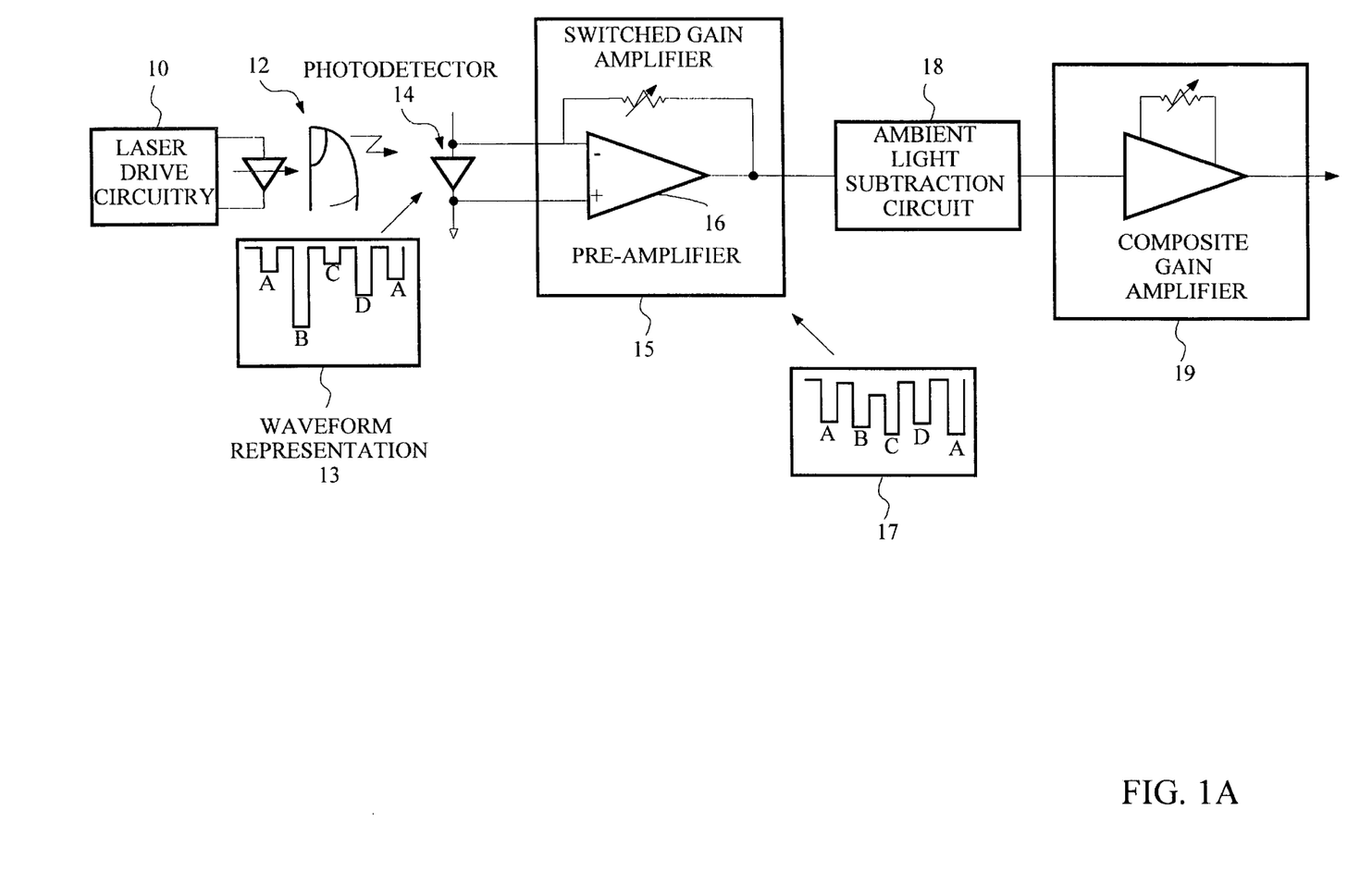
FIGS. 1A–1C diagram photoplethysmographic apparatus implementing the present invention.
Figure 1B:
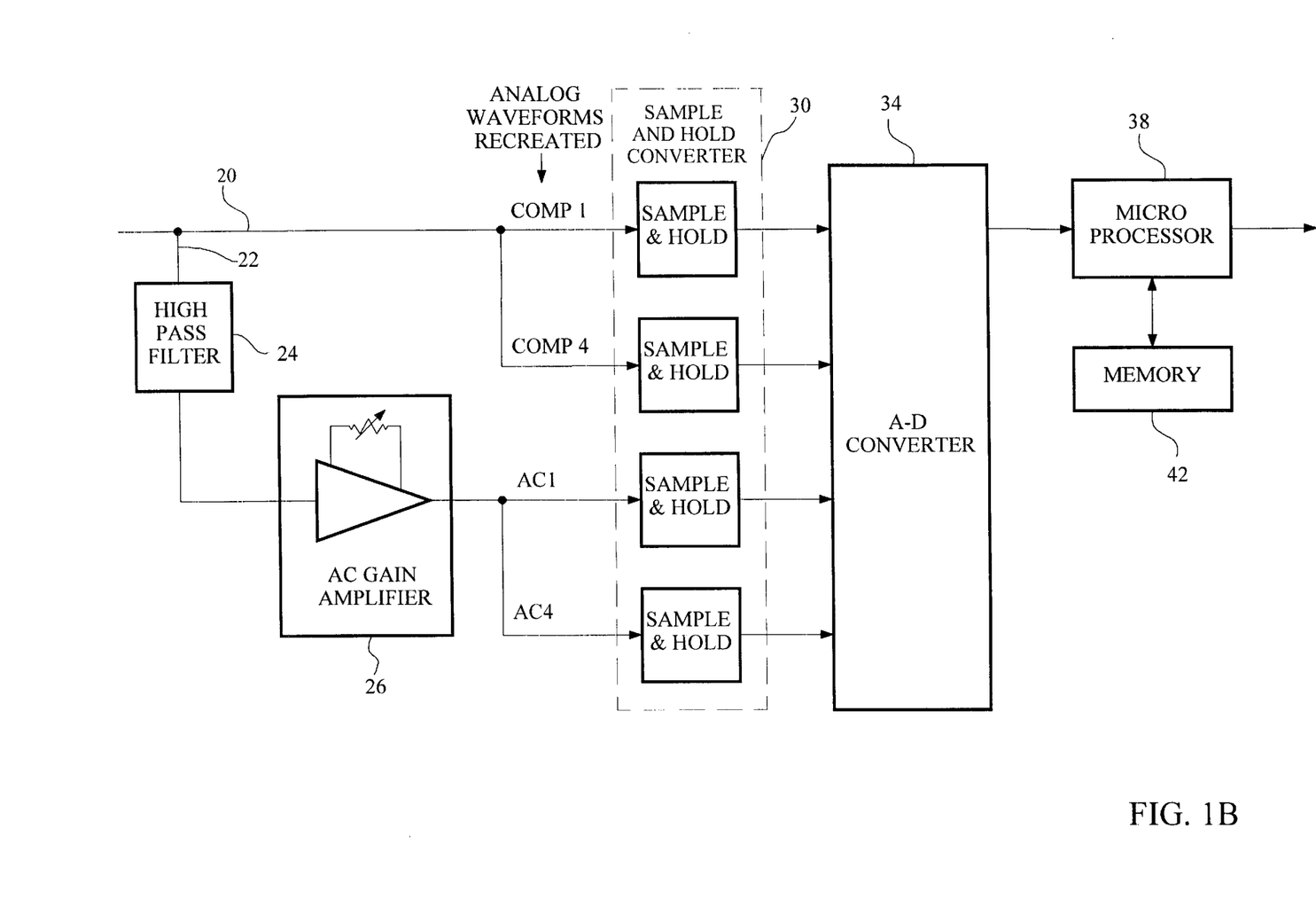
Figure 1C:
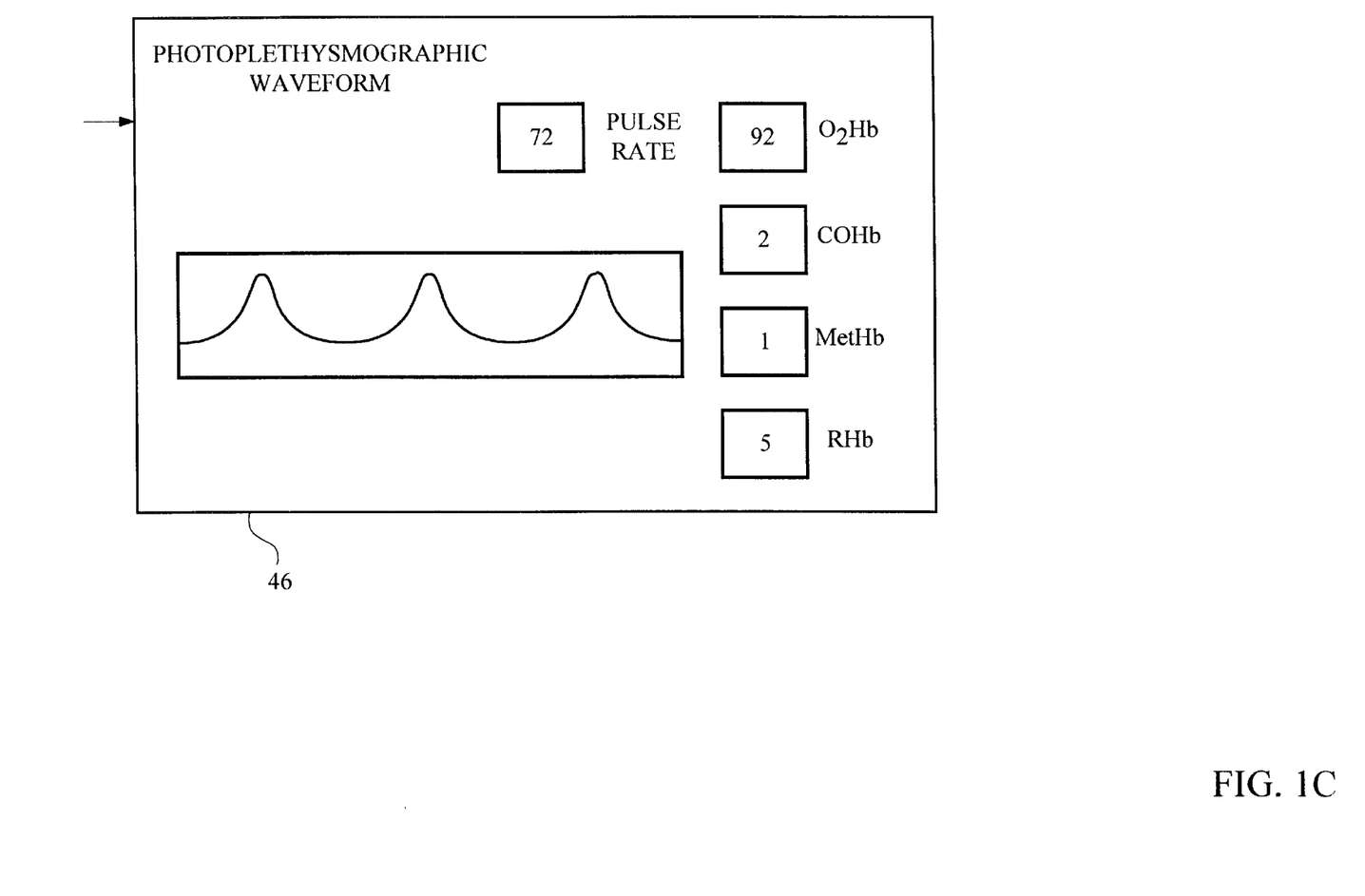

FIG. 1 shows one embodiment for a photoplethysmographic apparatus implementing the present invention. Laser drive circuitry 10 includes four laser diodes (not shown) that are time division multiplexed by the drive circuitry 10, each laser emitting light having a spectral content different from the other lasers. Moreover, each such laser is activated sequentially at a corresponding ⅛th duty cycle where the next ⅛ duty cycle after each laser activation is a time when all diodes are turned off or deactivated so that the apparatus can measure the ambient light levels (i.e., dark time). The light emitted by the laser diodes is directed at a tissue-under-test 12 which could be, for example, a finger or earlobe when measurements of light transmitted through the tissue-under-test are to be obtained. Alternatively, the tissue-under-test 12 may be a forehead or cheek when measurements of the light reflected from the tissue-under-test are to be obtained. Assuming measurements of light transmitted through the tissue-under-test 12 are to be used, the intensity of the light transmitted through the tissue-under-test 12 is represented by waveform representation 13. The letters A through D each refer to a specific light intensity transmitted through the tissue-under-test 12 by a corresponding one of the laser diodes activated during its corresponding duty cycle. The photodetector 14 receives the transmitted light and converts it into a current which is passed along to a switched gain amplifier 15. The switched gain amplifier 15 amplifies each current resulting from an activation of one of the laser diodes, and each such current is amplified at its own individual gain. The preamplifier 16, included in the switched gain amplifier 15 is also a transimpedence amplifier that converts the current out of the photodetector 14 into a voltage level. This voltage level output is illustrated in waveform representation 17, and this output is passed on to the ambient light subtraction circuit 18 which subtracts, for each laser diode, the associated signals from its deactivation time from each of the signals for its activation time, thereby leaving only the information attributable to the activation time signal. This information is passed on to the composite gain amplifier 19 which further increases the amplitude of these time division multiplexed signals. The output for each laser diode from the composite gain amplifier 19, is split into two separate paths. One path is denoted the composite path 20, and the other is denoted the AC path 22. Signals on the AC path 22 first go through the high pass filter 24 and then go through to the AC gain amplifier 26. One result of the split paths 20 and 22 is that through the use of various filters, as one skilled in the art will understand, eight analog waveforms are created and these waveforms are subsequently passed into a sample-and-hold converter 30. Accordingly, for each laser diode activation, the sample-and-hold converter 30 holds a composite value (e.g. from COMP 1, COMP 2, COMP 3 and COMP 4) as well as an AC value (e.g. from AC 1, AC 2, AC3 and AC4), wherein each AC value is a composite signal with the DC offset removed by the high pass filter 24 and the remaining AC signal gained up by the AC gain amplifier 26. Finally, the information deposited into the sample and hold converter 30 is passed along into the analog to digital converter 34 where the analog information is converted into digital values. The resulting digital values are then sent to the microprocessor 38 which stores these values in the memory 42. It is these values that the microprocessor 38 uses for computing the blood analyte values by the present invention so that the results can be sent to the display module 46 for output to the user. The four hemoglobin values shown on the right hand side of the display module 46 are illustrations of analyte values computed by the present invention.

Figure 2:
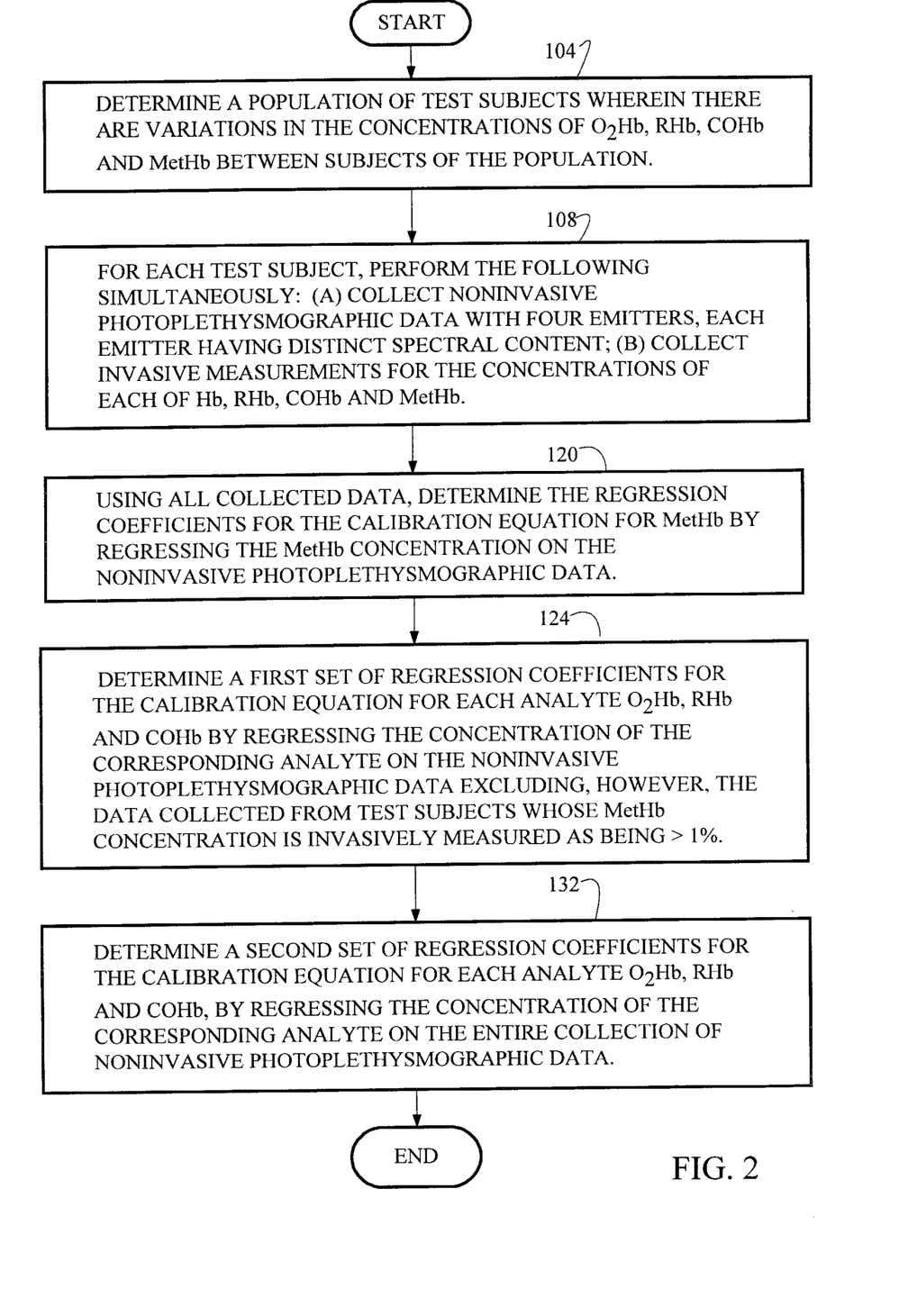
FIG. 2 is a high level flowchart of the steps performed in obtaining regression coefficients used for estimating concentrations of various species of hemoglobin in blood such as MetHb, $O_2Hb$, RHb and COHb.

The flowchart of FIG. 2 describes the high level steps performed in determining various sets of calibration coefficients for subsequently estimating the concentrations of MetHb, $O_2Hb$, RHb and COHb according to the present invention. In particular, in step 104 a population of test subjects is determined, wherein there are variations in the concentrations of $O_2Hb$, RHb, COHb, and MetHb between subjects. Preferably, the variations should be substantially similar to the variations in the general population. In step 108, for each test subject, simultaneously collect: (a) noninvasive photoplethysmographic data from each of the four emitters, and (b) invasive measurements for the concentrations of each of $O_2Hb$, RHb, COHb and MetHb. In particular, for the noninvasive photoplethysmographic data, measurements of the different spectral contents are obtained from each of the four channels, wherein the four center wavelengths corresponding to these channels may be, for example, 632 nm, 671 nm, 813 nm and 957 nm.

Subsequently, in steps 120, 124 and 132, three collections of calibration coefficients are obtained for a particular calibration equation such as equation (4). Accordingly, in step 120, regression coefficients are determined for MetHb using the corresponding photoplethysmographic data and invasive MetHb concentration measurements for each of the test subjects. In particular, the invasive MetHb measurements are statistically correlated with the photoplethysmographic data, where the calibration coefficients are chosen to give the smallest possible estimation error (as in least squares regression).

Further note that in step 120, the concentrations of the other species of hemoglobin are ignored. MetHb yields spectral content measurements that are sufficiently dominant between 600–1000 nm so that it can be accurately measured regardless of the concentrations of $O_2Hb$, RHb, and COHb. Therefore, MetHb is the analyte contained in the first collection of the present invention.

In step 124, calibration coefficients for the particular calibration equation are determined for the analytes $O_2Hb$, RHb, and COHb. However, instead of using all of the data collected, this step excludes data collected where the MetHb concentration is invasively measured as greater than It. That is, in one embodiment, the concentrations of each of $O_2Hb$, RHb and COHb are determined from equation (4), where the constants $a_i$, $b_i$, i=1, 2, 3, 4, are estimated through least squares regression. It is important to note that the regression process for this step uses only photoplethysmographic data where the concentration of MetHb (invasively measured) is between 0.0% to 1%. However, other ranges are also within the scope of the present invention. It is important also to note that in this case three analyte concentrations are being calibrated at four different center wavelengths, so the system is over-determined and regression may be used to obtain regression coefficients that when used in equation (4) yields more accurate concentration measurements than regression coefficients obtained by using an exactly-determined system (i.e., calibrating four analytes using four distinct center wavelengths).

In step 132, an alternative set of calibration coefficients to those of step 124 is determined, wherein for each analyte O₂Hb, RHb and COHb, regression coefficients are determined for the particular calibration equation form (e.g., equation (4),) using all the data collected regardless of MetHb concentration. Thus, note that there are two sets of regression coefficients for the analytes O₂Hb, RHb and COHb, one set derived from data for a subset of the test population and one set derived from data for the entire test population, wherein the set of regression coefficients from the subset of the test population is believed to provide more accurate analyte concentration estimates when the patient's MetHb concentration is less than 1%.

Figure 3:
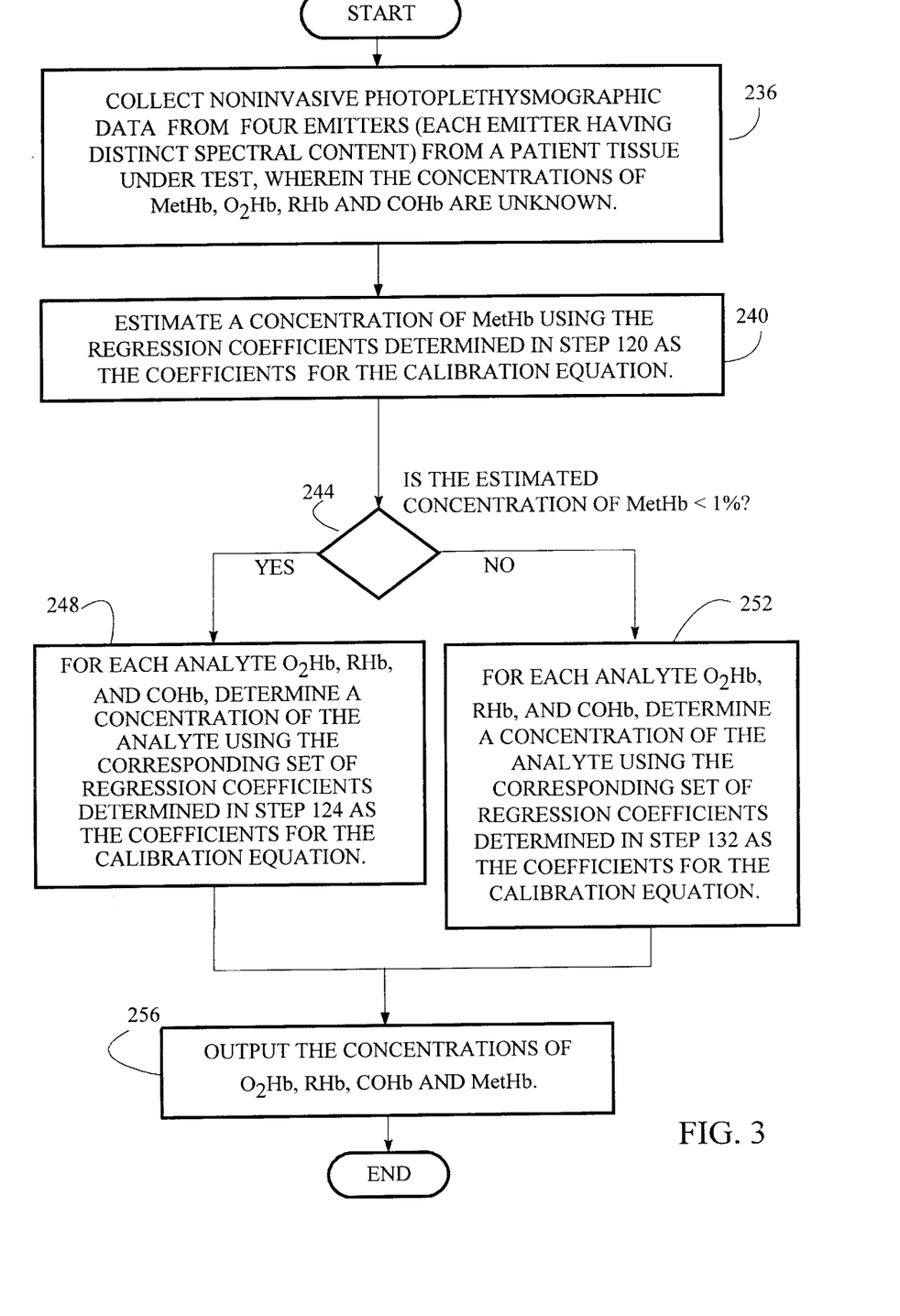
FIG. 3 is a high level flowchart of the steps performed in using the regression coefficients obtained according to the steps of FIG. 2, for estimating the concentrations of MetHb, $O_2Hb$, RHb and COHb in a tissue-under-test.

Referring now to FIG. 3, a flowchart is presented illustrating the steps that are performed when using the present invention to noninvasively estimate the concentrations of unknown amounts of MetHb, O₂Hb, RHb and COHb. Accordingly, in step 236, noninvasive photoplethysmographic data for a patient tissue-under-test is collected from the four emitters. In step 240, an estimate of the concentration of MetHb is obtained using the regression coefficients determined in step 120 of FIG. 2. That is, the same calibration equation of step 120 is used with the regression coefficients determined in step 120 and the differential absorptions $dA_i$, i=1, 2, 3, 4. Subsequently, in step 244, a determination is made as to whether the estimated concentration of MetHb is less than 1%. If so, then by assuming that the estimated concentration of MetHb is the actual concentration, each of the analytes O₂Hb, RHb and COHb are determined by using the calibration coefficients obtained in step 124. Alternatively, if in step 240, the estimated concentration of MetHb is determined to be greater than or equal to 1%, then step 252 is performed where the concentrations of the analytes O₂Hb, RHb and COHb are determined using the calibration coefficients determined in step 132. Finally, in step 256, the estimated concentrations of the four analytes are output.

The above embodiment of the present invention can be readily generalized. In particular, the present invention may be used measure any analytes with the following properties: (1) a first collection of analytes has absorbance characteristics at the center wavelengths being used that are so distinct from one another and from the remaining analytes that they may be very accurately measured regardless of the concentrations of other analytes, and (2) by constraining analytes in the first collection to some predetermined ranges, analytes in the remaining collection may be accurately calibrated and, hence, measured.

Moreover, the method of the present invention is also applicable to initially over-determined systems. In particular, as one skilled in the art will understand; if the initial number of center wavelengths used is greater than the number of analytes to be measured, then the initial system is over-determined instead of exactly determined as in the above embodiment. In this case, the present invention may be used to further increase the number of center wavelengths used as compared to analytes being measured, thereby increasing measurement accuracy.

Further, it is within the scope of the present invention to utilize any one of a number of statistical regression analysis techniques with or in place of the nonlinear least squares techniques in the above embodiments. In particular, the following techniques are also within the scope of the present invention: linear least squares regression, partial least squares regression, principle component regression, latent root regression, Fourier regression and ridge regression.

It is also within the scope of the present invention to utilize more than two sets of regression coefficients for estimating the concentrations of analytes such as O₂Hb, RHb and COHb. That is, instead of a first set of regression coefficients for MetHb concentrations less than 1% and a second set for MetHb concentrations greater than or equal to 1%, a different set of regression coefficients may be provided for, e.g., each of the MetHb concentration ranges: 0 to less than 5%, 5% to less than 10%, and greater than or equal to 10%.

The foregoing discussion of the invention has been presented for purposes of illustration and description. Further, the description is not intended to limit the invention to the form disclosed herein. Consequently, variation and modification commensurate with the above teachings, within the skill and knowledge of the relevant are, are within the scope of the present invention. The embodiment described hereinabove is further intended to explain the best mode presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

What is claimed is:

1. An apparatus for performing spectrophotometric analyte concentration measurement comprising:

means for communicating beams of light each having a distinct spectral content across a tissue sample for obtaining values related to a measurement of the concentration of each of a plurality of analytes in the tissue sample;

means for measuring the beams of light received across the tissue sample for obtaining light measurements;

first estimating means for estimating a concentration of a collection of at least one of said plurality of analytes using said measured light measurements;

means for determining whether said first estimated concentration for each of the analytes in the collection satisfies a predetermined one or more constraints; and second estimating means for estimating a concentration of the remaining analytes of said plurality of analytes when said means for determining indicates that said predetermined one or more constraints have been met;

wherein said second estimating means determines an estimated measurement of the remaining analytes using said measured light and using said first estimated concentration as a substantially exact measurement of said collection of analytes.

2. An apparatus as claimed in claim 1, wherein the means for communicating light comprises a plurality of emitters each emitting light having a spectral content characterized by a distinct center wavelength.

3. An apparatus as claimed in claim 2, wherein each said distinct center wavelength is in a range of 600 nanometers to 1000 nanometers.

4. An apparatus as claimed in claim 2, wherein said emitter is a laser diode.

5. An apparatus as claimed in claim 1, wherein the measurement of each of said plurality of analytes is a concentration of the analyte in the blood of the tissue sample.

6. An apparatus as claimed in claim 1, wherein said plurality of analytes is selected from the group consisting of: methemoglobin, oxyhemoglobin, deoxyhemoglobin and carboxyhemoglobin.

7. An apparatus as claimed in claim 1, wherein said means for determining determines whether said first estimated concentration satisfies a constraint that said first estimated concentration is less than a predetermined concentration in the tissue sample.

8. An apparatus as claimed in claim 1, wherein said collection of at least one of said plurality of analytes includes only methemoglobin.

9. An apparatus as claimed in claim 8, wherein said means for determining determines whether methemoglobin is less than approximately one percent of a total amount of hemoglobin in the blood of the tissue sample.

10. An apparatus as claimed in claim 1, further including a third estimating means for estimating a concentration of at least one of said remaining analytes, wherein said third estimating means is used when said means for determining determines that an estimated concentration for one or more analytes in said collection does not satisfy one of said predetermined one or more constraints.

11. An apparatus as claimed in claim 10, wherein said third estimating means uses regression coefficients for estimating the remaining analytes, wherein said regression coefficients are the result of a statistical calibration on an exactly determined system.

12. An apparatus as claimed in claim 1, wherein said remaining analytes are selected from the group consisting of: oxyhemoglobin, deoxyhemoglobin and carboxyhemoglobin.

13. An apparatus as claimed in claim 1, wherein the total number of said distinct spectral contents of said communicated light is one of: (a) equal to the total number of analytes in said plurality of analytes, and (b) greater than the total number of analytes in said plurality of analytes.

14. An apparatus as claimed in claim 1, wherein said first estimating means determines an estimate of the concentration of said collection using regression coefficients.

15. An apparatus as claimed in claim 14, wherein said regression coefficients are determined using one of: least squares regression, partial least squares regression, principle component regression and Fourier regression.

16. A method for determining regression coefficients for a photoplethysmographic analyte measurement system, comprising:

first collecting noninvasive photoplethysmographic data from a plurality of test subjects using a predetermined number of light emitters, each said light emitter providing a distinct spectral content of light;

second collecting invasive concentration measurements for each of a plurality of blood analytes from each of the test subjects;

determining a first set of regression coefficients, wherein said first set:
(A) has regression coefficients for each analyte of a first collection of said plurality of analytes, said first collection including at least a first analyte; and
(B) is determined using at least one of: (a) said noninvasive photoplethysmographic data, and (b) at least some of said invasive concentration measurements;

determining a second set of regression coefficients, said second set having regression coefficients for each analyte of a second collection of said remaining analytes not in said first collection, wherein (a) said second set is determined using at least a subcollection of said noninvasive photoplethysmographic data, and (b) said subcollection satisfies a predetermined constraint related to a concentration measurement of said first analyte obtained in said second collecting step; and determining a third set of regression coefficients, said third set having regression coefficients for each analyte of said second collection using substantially all of said noninvasive photoplethysmographic data.

17. A method as claimed in claim 16, wherein, for each of said plurality of test subjects, said steps of first collecting and second collecting are performed substantially simultaneously on the test subject for obtaining corresponding noninvasive photoplethysmographic data and invasive concentration measurements.

18. A method as claimed in claim 17, wherein said predetermined constraint excludes at least some of said noninvasive photoplethysmographic data for a test subject having a corresponding invasive concentration measurement outside of a predetermined range.

19. A method as claimed in claim 18, wherein said predetermined range is between zero and approximately 1% when said first analyte is MetHb.

20. A method as claimed in claim 16, wherein each of said first, second and third sets of regression coefficients is determined using one of: a least squares regression, a partial least square regression, a principle component regression and a Fourier regression.

21. A method as claimed in claim 16, wherein said first collection includes MetHb and said remaining collection includes $O_2Hb$, RHb, and COHb.

22. A method for photoplethysmographic determination of analyte concentrations in a tissue comprising:

directing a plurality of beams of light through the tissue wherein each beam of light is characterized by a distinct spectral content;

measuring the light transmitted through the tissue;

estimating concentrations for at least one analyte in a first collection of a plurality of analytes using said light measurements;

comparing said estimated concentrations for the at least one analyte in said first collection with a predetermined criteria for said estimated initial concentrations;

if said estimated concentrations of said first collection of analytes satisfies said criteria then estimating a concentration for each of the remaining analytes not in said first collection of analytes using said light measurements and said estimated concentrations of said first collection of analytes as a substantially accurate estimate of the actual analyte concentration.

23. A method as claimed in claim 22, wherein said first collection of analytes comprises MetHb and said remaining collection of analytes is selected from the group consisting of: $O_2Hb$, Rhb and CoHb.

24. A method as claimed in claim 22, wherein the spectral content of each beam of light is characterized by a distinct center wavelength.

* * * * *